United States Patent
Su

(10) Patent No.: US 8,658,828 B2
(45) Date of Patent: Feb. 25, 2014

(54) RECOVERY OF TOLUENE DIAMINE FROM TAR WASTE RESIDUE DISCHARGED FROM SYNTHESIS PROCESS OF TOLUENE DIISOCYANATE

(75) Inventor: Deshui Su, Cangzhou (CN)

(73) Assignee: Cangzhou Fengyuan Environmental Protection Science and Technology Co., Ltd., Cangzhou Hebei (CN)

( * ) Notice: Subject to any disclaimer, the term of this patent is extended or adjusted under 35 U.S.C. 154(b) by 0 days.

(21) Appl. No.: 13/639,768

(22) PCT Filed: Dec. 19, 2011

(86) PCT No.: PCT/CN2011/084196
§ 371 (c)(1),
(2), (4) Date: Oct. 5, 2012

(87) PCT Pub. No.: WO2012/100609
PCT Pub. Date: Aug. 2, 2012

(65) Prior Publication Data
US 2013/0041182 A1 Feb. 14, 2013

(30) Foreign Application Priority Data
Jan. 27, 2011 (CN) .......................... 2011 1 0029377

(51) Int. Cl.
*C07C 209/00* (2006.01)
(52) U.S. Cl.
USPC ........................................................ 564/437
(58) Field of Classification Search
None
See application file for complete search history.

(56) References Cited

U.S. PATENT DOCUMENTS

| | | |
|---|---|---|
| 3,128,310 A | 4/1964 | Koch |
| 3,331,876 A | 7/1967 | Horn et al. |
| 3,499,021 A | 3/1970 | Kober et al. |
| 3,636,030 A | 1/1972 | Perkins |
| 3,694,323 A | 9/1972 | Cooper et al. |
| 4,000,099 A | 12/1976 | Nemoto et al. |
| 4,143,008 A | 3/1979 | Zwolinski et al. |
| 4,311,800 A | 1/1982 | Reischl |
| 5,804,648 A | 9/1998 | Slack |

FOREIGN PATENT DOCUMENTS

| | | |
|---|---|---|
| CN | 1802344 A | 7/2006 |
| DE | 1962598 A1 | 7/1970 |
| DE | 2942678 A1 | 5/1981 |
| DE | 257827 A1 | 6/1988 |
| DE | 296088 A5 | 11/1991 |
| DE | 4211774 A1 | 10/1993 |
| JP | 58-201751 A | 11/1983 |
| WO | 1999/65868 A1 | 12/1999 |
| WO | 00/68180 A1 | 11/2000 |
| WO | 2004/108656 A1 | 12/2004 |

OTHER PUBLICATIONS

State Intellectual Property Offic of the P.R. China, International Seach Report in application No. PCT/CN2011/084196, dated Mar. 15, 2012.

*Primary Examiner* — Johann Richter
*Assistant Examiner* — Clinton Brooks
(74) *Attorney, Agent, or Firm* — Kenyon & Kenyon LLP

(57) ABSTRACT

The recovery of toluene diamine from tar waste residues discharged from the synthesis process of toluene diisocyanate comprising steps of: a) grinding the tar waste residues into particles; b) dispersing the particles of tar waste residues into a phase transfer catalyst, alkali and water to obtain a slurry, said phase transfer catalyst being selected from the group consisting of higher alcohols, polyols, polyether compounds and combinations thereof having a boiling point ranging from 120 to 280° C.; c) under the protection of a protective gas, subjecting the slurry to a hydrolysis reaction at a temperature of 120-180° C. under a meter-measured pressure of 0-0.95 MPa to produce toluene diamine; and d) recovering toluene diamine from the hydrolysis reaction solution. The present invention achieves highly efficient recovery of toluene diamine (the recovery rate of TDA is up to 60%) under mild conditions such as 120-180° C. and 0-0.95 MPa (meter-measured pressure), and has a significant economic benefit and friendliness to the environment by recycling the phase transfer catalyst (its recovery rate is up to 99.6%) and water.

11 Claims, No Drawings

RECOVERY OF TOLUENE DIAMINE FROM TAR WASTE RESIDUE DISCHARGED FROM SYNTHESIS PROCESS OF TOLUENE DIISOCYANATE

This application is a 371 U.S. national phase application of International Application No. PCT/CN2011/084196, filed on Dec. 19, 2011, which claims the benefit of Chinese Patent Application No. 201110029377.6 filed on Jan. 27, 2011, the disclosures of which are herein incorporated by reference.

TECHNICAL FIELD

The present invention relates to a method of recovering and preparing toluene diamine (TDA) by hydrolyzing high boiling point tar waste residues or solid distillation remains discharged from the synthesis process of toluene diisocyanate (TDI) under mild conditions.

BACKGROUND TECHNOLOGY

TDI is an important material for producing polyurethane, which is mainly used as the material and intermediate for polyurethane soft foams, rigid foams, adhesives, coatings, sealants and a series of elastomers. TDA, as an essential material for preparing TDI and an important material for preparing a variety of dyes and medical intermediates, also has a broad market prospect.

At the end of the synthesis process of TDI, TDI is usually isolated from the product mixture by means of a rectification method. High boiling point solid residues or distillation remains discharged from the fraction at the bottom of the rectification column upon drying are generally called tar powder. The tar powder is a mixture consisting of polybiuret, byproducts and a plurality of impurities.

The prior art has described various methods of directly utilizing the substances in the distillation remains discharged from the synthesis process of TDI. In U.S. Pat. No. 3,499,021, the distillation remains are subjected to phosgenation treatment and returned to the process. In DE4211774, DD257827 and U.S. Pat. No. 3,694,323, the distillation remains are mixed with diphenylmethane diisocyanate (MDI), and partially distilled and transformed into polyurethane. DD296088, U.S. Pat. No. 4,143,008, U.S. Pat. No. 4,000,099 and U.S. Pat. No. 4,311,800 describe that the distillation remains are directly reacted with polyols to form corresponding polyurethane for the preparation of synthetic resins, lignocelluloses, and the like. However, the additional value of the products obtained by these processes is not high, and they consume a large amount of alcohols (the alcoholysis reaction requires to consume at least 24% of polyols), and have a high cost.

Another way to utilize the distillation remains is to hydrolyze them. It is a well-known technique to hydrolyze TDI tar powder by using the alkaline aqueous solution added with ammonia water and alkaline earth hydroxide, or the acid aqueous solution of inorganic and organic acids so as to prepare TDA. However, the tar powder has special physiochemical properties and is hardly soluble in both water and organic solvents, the hydrolysis thereof belongs to non-homogeneous reactions, and the process of transferring mass and heat is slow, thus the speed of the hydrolysis reaction under normal temperature and pressure is extremely slow and the yield thereof is very low.

Although the yield of TDA can be increased by the methods of increasing the hydrolysis temperature and pressure and improving the way to mix and contact the materials, the extent of the yield increase is limited due to the restrictions by the low boiling point of water and poor water solubility of the reactants, thus the practicability is quite poor. The reports in this respect can be found in U.S. Pat. No. 3,331,876, U.S. Pat. No. 3,128,310, DE2942678, DE1962598 and JP58-201751. In addition, the hydrolysis technique introduced by the Korean patent 2001-52948 adopts a continuous or semi-continuous reverse-mixing reactor, which improves the efficiency of mass transfer to some extent, but just increases the degree of mechanical mixing instead of improving the activities of the reactants. It is still difficult to get rid of the restriction by the resistance to mass transfer and thus has little effect.

Use of subcritical water or supercritical water hydrolysis may further improve the hydrolysis temperature and pressure, speed up the reaction, and increase the yield of TDA. The Korean patent 2001-1488 discloses a method in which ammonia water is used as a catalyst for the hydrolysis of tar waste materials and the hydrolysis is conducted in supercritical water at 350-600° C. under 218-400 atmospheric pressures. Although the high temperature and pressure conditions of the supercritical water can speed up the hydrolysis, the supercritical water not only causes the device to corrode, but also decreases the solubility of various salts; and moreover, ammonium hydrocarbonate, ammonium carbonate and organic polyamine salt as well as composite hydrate salts transformed from partial ammonia water during the hydrolysis process would all cause the problems such as blocking in pipelines of the device and secondary pollution in the environment.

The Chinese patent CN200480015939.X makes a series of improvements to the supercritical hydrolysis of tar waste materials, the hydrolysis product of toluene diisocyanate (TDA) has a notably-increased yield and can be returned back to the TDI production process, and its hydrolysis catalyst of carbonate and water can be recycled by means of the recovery. Said invention selects alkaline earth hydroxide or carbonate as a catalyst, which can avoid the problems brought by the catalyst of ammonia water, but still does not solve the problems of poor solubility of the reactants in water and difficulty in transferring mass, thus the invention still adopts the supercritical hydrolysis under high temperature and pressure (100-200 atmospheric pressures, temperature of 280-320° C.). Accordingly, it is difficult to get rid of the problems of high requirement and investment on the device, production security being difficult to guarantee, and blocking in pipelines of the device brought therefrom, thus the industrialization is hard to realize.

Based on the above problems, the preparation of TDA from TDI distillation remains are not implemented at an industrial-scale yet, thereby resulting in that most of the TDI distillation remains currently have to be burned at a high temperature, which not only causes waste in a large amount of resources but also can hardly avoid secondary pollution.

The treatment of tar powder with a hydrolysis method can greatly reduce the amount of TDI distillation remains to be burned, can recover and utilize TDA with a high additional value from the waste, thereby achieves the purpose of energy saving, emission reduction and resource recycling in the isocyanate industry, however, the preparation of TDA by hydrolyzing TDI tar waste residues belongs to non-homogeneous reactions, the hydrolysis at a temperature lower than 250° C. would lead to the deficiencies in large resistance to mass transfer and poor activity of the reaction, while the hydrolysis at a temperature higher than 400° C. would cause the problem that the target product TDA is easily pyrolyzed. This results in that the existing methods involve the following problems: it is difficult to raise the temperature for the hydrolysis reaction due to the restriction by the low boiling point of the hydrolysis medium, the efficiency of the hydrolysis is poor; choosing an inappropriate catalyst causes the tar powder to transform into organic salts with a low value, recycling of resources cannot be realized; using an excess amount of water, waste water or nitrogen components contained in discarded substances causes secondary pollution; the method under high temperature and pressure may increase the hydrolysis yield to some extent, however, the investment in the device for supercritical hydrolysis is high, and the operation security thereof cannot be guaranteed, it is hard to realize real industrialized production; the alcoholysis process consumes a large amount of alcohols, the target product does not have a high value; the yield of TDA is extremely low when it is prepared through the hydrolysis after the alcoholysis, the economic applicability is poor. Consequently, direct preparation of TDA by hydrolyzing TDI process tar waste residues is quite difficult, the prior art can hardly meet the requirement of the industrialization.

SUMMARY OF THE INVENTION

The objective of the present invention is to recover TDA from tar waste residues discharged from the synthesis process of TDI under mild conditions.

According to the present invention, a method of recovering TDA from tar waste residues discharged from the synthesis process of TDI is provided, which comprising steps of
  a) grinding the tar waste residues into particles;
  b) dispersing the particles of tar waste residues into a phase transfer catalyst, alkali and water to obtain a slurry, said phase transfer catalyst being selected from the group consisting of higher alcohols, polyols, polyether compounds and combinations thereof having a boiling point ranging from 120 to 280° C.;
  c) under the protection of a protective gas, subjecting the slurry to a hydrolysis reaction at a temperature of 120-180° C. under a meter-measured pressure of 0-0.95 MPa to produce TDA; and
  d) recovering TDA from the hydrolysis reaction solution.

Preferably the tar waste residues are ground into particles below 100 meshes.

The protective gas is preferably nitrogen gas.

The time for the hydrolysis reaction may be 8 to 16 hours.

The alkali may be sodium hydroxide or potassium hydroxide, or may be sodium carbonate or potassium carbonate.

The pH value of the slurry is preferably not less than 10.

Preferably, in the slurry, the weight percentage of the particles of tar waste residues is 10-30%, the weight percentage of the phase transfer catalyst is 40-75%, the weight percentage of the alkali is 10-30%, and the weight percentage of water is 0-25%.

Preferably, the phase transfer catalyst is selected from the group consisting of heptanol, diethylene glycol, glycol, 1,2-propanediol, 1,3-propanediol, 1,4-butanediol, hexanediol and combinations thereof.

The step d) may include: thermally filtering the hydrolysis reaction solution to remove solid precipitates, then passing it through a first distillation column to isolate a first gas-phase overhead fraction and a first bottom fraction, the first gas-phase overhead fraction containing water vapor and light weight gaseous components, and the first bottom fraction containing a phase transfer catalyst, TDA and coal tar having a high boiling point; finally isolating TDA from the first bottom fraction by means of reduced pressure distillation.

The reduced pressure distillation may include: passing the first bottom fraction through a second reduced pressure distillation column to isolate a second gas-phase overhead fraction and a second bottom fraction, the second gas-phase overhead fraction containing a phase transfer catalyst, and the second bottom fraction containing TDA and coal tar having a high boiling point; and isolating TDA from the second bottom fraction.

The step of isolating TDA from the second bottom fraction may include: passing the second bottom fraction through a third distillation column to isolate a third gas-phase overhead fraction and a third bottom fraction, the third overhead fraction containing TDA, and the third bottom fraction containing coal tar having a high boiling point.

The phase transfer catalyst isolated from the second reduced pressure distillation column is preferably recycled.

The water vapor contained in the first gas-phase overhead fraction is preferably recycled after being condensed.

The hydrolysis reaction may be conducted in two or more reactors connected in series or in parallel. The hydrolysis reaction may also be conducted in a reactor which can be heated at a controllable temperature, in a stirring-allowable reactor, and/or in a sealed reactor or a reactor having a recirculation device.

The present invention greatly improves the speed of the hydrolysis of tar powder, achieves highly efficient recovery of TDA (the recovery rate of TDA is up to 60%) under mild conditions such as 120-180° C. and 0-0.95 MPa (meter-measured pressure), and has a significant economic benefit and friendliness to the environment by recycling the phase transfer catalyst (its recovery rate is up to 99.6%) and water.

SPECIFIC EMBODIMENTS

The present invention will be better understood through the following examples, which, however, cannot be understood as any limitation to the scope of the present invention.

Example 1

TDI tar solid waste residue particles, diethylene glycol, sodium hydroxide and water are mixed by a weight ratio of 10:75:10:5. Under stirring, after exhausting air by inputting nitrogen gas, the mixture is recirculated (under a normal pressure, namely the meter-measured pressure is 0 MPa) and hydrolyzed at 180° C. for 10 hours. The mixed solution after the hydrolysis is thermally filtered to remove unreacted solid residues, salts and the like, and then passed through a first column to remove water vapor (which may be recycled after being condensed) and light weight gaseous components; diethylene glycol is recovered from a second column (the recovery rate thereof is 99.4%), and the product TDA is isolated from the overhead fraction in a third column, the yield of TDA is 58% (by weight) of the addition amount of waste residues.

Example 2

TDI tar solid waste residue particles, diethylene glycol, sodium hydroxide and water are mixed by a weight ratio of 10:75:10:5. Under stirring, after exhausting air by inputting nitrogen gas, the mixture is reacted at 180° C. in a sealed reaction vessel (0.95 MPa) for 10 hours. The other steps are identical with those in Example 1. Wherein the recovery rate of diethylene glycol is 99.5%, and the yield of TDA is 60% (by weight) of the addition amount of waste residues.

Example 3

TDI tar solid waste residue particles, diethylene glycol and potassium hydroxide are mixed by a weight ratio of 15:70:15.

Under stirring, after exhausting air by inputting nitrogen gas, the mixture is recirculated (normal pressure) and reacted at 180° C. for 10 hours. The other steps are similar to those in Example 1. Wherein the recovery rate of diethylene glycol is 99.2%, and the yield of TDA is 53% (by weight) of the addition amount of waste residues.

Example 4

TDI tar solid waste residue particles, diethylene glycol and potassium hydroxide are mixed by a weight ratio of 15:70:15. Under stirring, after exhausting air by inputting nitrogen gas, the mixture is reacted at 180° C. in a sealed reaction vessel (0.15 MPa) for 10 hours. The other steps are similar to those in Example 1. Wherein the recovery rate of diethylene glycol is 99.3%, and the yield of TDA is 55% (by weight) of the addition amount of waste residues.

Example 5

TDI tar solid waste residue particles, 1,2-propanediol, potassium hydroxide and water are mixed by a weight ratio of 20:60:15:5. Under stirring, after exhausting air by inputting nitrogen gas, the mixture is recirculated and hydrolyzed at 140° C. for 12 hours. The other steps are identical with those in Example 1. Wherein the recovery rate of 1,2-propanediol is 99.0%, and the yield of TDA is 41% of the addition amount of waste residues.

Example 6

TDI tar solid waste residue particles, 1,2-propanediol, potassium hydroxide and water are mixed by a weight ratio of 20:60:15:5. Under stirring, after exhausting air by inputting nitrogen gas, the mixture is reacted at 140° C. in a sealed reaction vessel (0.3 MPa) for 12 hours. The other steps are identical with those in Example 1. Wherein the recovery rate of 1,2-propanediol is 99.2%, and the yield of TDA is 42% of the addition amount of waste residues.

Example 7

TDI tar solid waste residue particles, 1,2-propanediol and potassium hydroxide are mixed by a weight ratio of 20:60:20. Under stirring, after exhausting air by inputting nitrogen gas, the mixture is recirculated (normal pressure) and reacted at 130° C. for 10 hours. The other steps are similar to those in Example 1. Wherein the recovery rate of 1,2-propanediol is 98.7%, and the yield of TDA is 39% of the addition amount of waste residues.

Example 8

TDI tar solid waste residue particles, 1,2-propanediol and potassium hydroxide are mixed by a weight ratio of 20:60:20. Under stirring, after exhausting air by inputting nitrogen gas, the mixture is reacted at 130° C. in a sealed reaction vessel (0.15 MPa) for 10 hours. The other steps are similar to those in Example 1. Wherein the recovery rate of 1,2-propanediol is 98.9%, and the yield of TDA is 38% of the addition amount of waste residues.

Example 9

TDI tar solid waste residue particles, 1,3-propanediol, sodium hydroxide and water are mixed by a weight ratio of 15:45:15:25. Under stirring, after exhausting air by inputting nitrogen gas, the mixture is recirculated and hydrolyzed at 160° C. for 8 hours. The other steps are identical with those in Example 1. Wherein the recovery rate of 1,3-propanediol is 98.3%, and the yield of TDA is 38% of the addition amount of waste residues.

Example 10

TDI tar solid waste residue particles, 1,3-propanediol, potassium hydroxide and water are mixed by a weight ratio of 15:45:15:25. Under stirring, after exhausting air by inputting nitrogen gas, the mixture is reacted at 160° C. in a sealed reaction vessel (0.55 PMa) for 12 hours. The other steps are identical with those in Example 1. Wherein the recovery rate of 1,3-propanediol is 98.9%, and the yield of TDA is 44% of the addition amount of waste residues.

Example 11

TDI tar solid waste residue particles, 1,3-propanediol and sodium hydroxide are mixed by a weight ratio of 25:50:25. Under stirring, after exhausting air by inputting nitrogen gas, the mixture is recirculated (normal pressure) and reacted at 160° C. for 8 hours. The other steps are similar to those in Example 1. Wherein the recovery rate of 1,3-propanediol is 98.1%, and the yield of TDA is 37% of the addition amount of waste residues.

Example 12

TDI tar solid waste residue particles, 1,3-propanediol and sodium hydroxide are mixed by a weight ratio of 25:50:25. Under stirring, after exhausting air by inputting nitrogen gas, the mixture is reacted at 160° C. in a sealed reaction vessel (0.15 MPa) for 12 hours. The other steps are similar to those in Example 1. Wherein the recovery rate of 1,3-propanediol is 98.8%, and the yield of TDA is 43% of the addition amount of waste residues.

Example 13

TDI tar solid waste residue particles, glycol, sodium hydroxide and water are mixed by a weight ratio of 15:65:10:10. Under stirring, after exhausting air by inputting nitrogen gas, the mixture is recirculated (normal pressure) and hydrolyzed at 150° C. for 15 hours. The other steps are identical with those in Example 1. Wherein the recovery rate of glycol is 99.3%, and the yield of TDA is 57% of the addition amount of waste residues.

Example 14

TDI tar solid waste residue particles, glycol, sodium hydroxide and water are mixed by a weight ratio of 15:65:10:10. Under stirring, after exhausting air by inputting nitrogen gas, the mixture is reacted at 120° C. in a sealed reaction vessel (0.15 MPa) for 13 hours. The other steps are identical with those in Example 1. Wherein the recovery rate of glycol is 99.6%, and the yield of TDA is 49% of the addition amount of waste residues.

Example 15

TDI tar solid waste residue particles, glycol and sodium hydroxide are mixed by a weight ratio of 20:65:15. Under stirring, after exhausting air by inputting nitrogen gas, the mixture is recirculated (normal pressure) and reacted at 140°

C. for 15 hours. The other steps are similar to those in Example 1. Wherein the recovery rate of glycol is 99.0%, and the yield of TDA is 55% of the addition amount of waste residues.

Example 16

TDI tar solid waste residue particles, glycol and sodium hydroxide are mixed by a weight ratio of 20:65:15. Under stirring, after exhausting air by inputting nitrogen gas, the mixture is reacted at 140° C. in a sealed reaction vessel (0.15 MPa) for 13 hours. The other steps are similar to those in Example 1. Wherein the recovery rate of glycol is 99.1%, and the yield of TDA is 50% of the addition amount of waste residues.

Example 17

TDI tar solid waste residue particles, 1,4-butanediol, sodium hydroxide and water are mixed by a weight ratio of 30:40:25:5. Under stirring, after exhausting air by inputting nitrogen gas, the mixture is recirculated and hydrolyzed at 150° C. for 15 hours. The other steps are identical with those in Example 1. Wherein the recovery rate of 1,4-butanediol is 99%, and the yield of TDA is 42% of the addition amount of waste residues.

Example 18

TDI tar solid waste residue particles, 1,4-butanediol, potassium hydroxide and water are mixed by a weight ratio of 30:40:25:5. Under stirring, after exhausting air by inputting nitrogen gas, the mixture is reacted at 150° C. in a sealed reaction vessel (0.4 MPa) for 10 hours. The other steps are identical with those in Example 1. Wherein the recovery rate of 1,4-butanediol is 99.2%, and the yield of TDA is 38% of the addition amount of waste residues.

Example 19

TDI tar solid waste residue particles, 1,4-butanediol and sodium hydroxide are mixed by a weight ratio of 30:40:30. Under stirring, after exhausting air by inputting nitrogen gas, the mixture is recirculated (normal pressure) and hydrolyzed at 150° C. for 15 hours. The other steps are similar to those in Example 1. Wherein the recovery rate of 1,4-butanediol is 98.7%, and the yield of TDA is 41% of the addition amount of waste residues.

Example 20

TDI tar solid waste residue particles, 1,4-butanediol and potassium hydroxide are mixed by a weight ratio of 30:40:30. Under stirring, after exhausting air by inputting nitrogen gas, the mixture is reacted at 150° C. in a sealed reaction vessel (0.15 MPa) for 14 hours. The other steps are similar to those in Example 1. Wherein the recovery rate of 1,4-butanediol is 98.8%, and the yield of TDA is 40% of the addition amount of waste residues.

Example 21

TDI tar solid waste residue particles, hexanediol, sodium hydroxide and water are mixed by a weight ratio of 10:45:10:25. Under stirring, after exhausting air by inputting nitrogen gas, the mixture is recirculated and hydrolyzed at 130° C. for 11 hours. The other steps are identical with those in Example 1. Wherein the recovery rate of hexanediol is 99%, and the yield of TDA is 42% of the addition amount of waste residues.

Example 22

TDI tar solid waste residue particles, hexanediol, sodium hydroxide and water are mixed by a weight ratio of 10:45:10:25. Under stirring, after exhausting air by inputting nitrogen gas, the mixture is reacted at 130° C. in a sealed reaction vessel (0.2 MPa) for 9 hours. The other steps are identical with those in Example 1. Wherein the recovery rate of hexanediol is 99.1%, and the yield of TDA is 37% of the addition amount of waste residues.

Example 23

TDI tar solid waste residue particles, hexanediol and sodium hydroxide are mixed by a weight ratio of 25:50:25. Under stirring, after exhausting air by inputting nitrogen gas, the mixture is recirculated (normal pressure) and reacted at 130° C. for 11 hours. The other steps are similar to those in Example 1. Wherein the recovery rate of hexanediol is 98.7%, and the yield of TDA is 41% of the addition amount of waste residues.

Example 24

TDI tar solid waste residue particles, hexanediol and potassium hydroxide are mixed by a weight ratio of 20:50:30. Under stirring, after exhausting air by inputting nitrogen gas, the mixture is reacted at 130° C. in a sealed reaction vessel (0.15 MPa) for 9 hours. The other steps are similar to those in Example 1. Wherein the recovery rate of hexanediol is 98.8%, and the yield of TDA is 36% of the addition amount of waste residues.

Example 25

TDI tar solid waste residue particles, heptanol, sodium hydroxide and water are mixed by a weight ratio of 15:60:15:10. Under stirring, after exhausting air by inputting nitrogen gas, the mixture is recirculated and hydrolyzed at 120° C. for 16 hours. The other steps are identical with those in Example 1. Wherein the recovery rate of heptanol is 98.0%, and the yield of TDA is 35% of the addition amount of waste residues.

Example 26

TDI tar solid waste residue particles, heptanol, potassium hydroxide and water are mixed by a weight ratio of 15:60:15:10. Under stirring, after exhausting air by inputting nitrogen gas, the mixture is reacted at 120° C. in a sealed reaction vessel (0.15 MPa) for 16 hours. The other steps are identical with those in Example 1. Wherein the recovery rate of heptanol is 98.5%, and the yield of TDA is 36% of the addition amount of waste residues.

Example 27

TDI tar solid waste residue particles, 1:1 mixture of butanediol and hexanediol, sodium carbonate, and water are mixed by a weight ratio of 10:60:30:10. Under stirring, after exhausting air by inputting nitrogen gas, the mixture is reacted at 140° C. in a sealed reaction vessel (0.3 MPa) for 10 hours. The other steps are identical with those in Example 1.

Wherein the recovery rate of the mixed alcohol is 99.2%, and the yield of TDA is 43% of the addition amount of waste residues.

Example 28

TDI tar solid waste residue particles, 1:1 mixture of diethylene glycol and glycol, and sodium carbonate are mixed by a weight ratio of 20:65:15. Under stirring, after exhausting air by inputting nitrogen gas, the mixture is recirculated (normal pressure) and reacted at 140° C. for 14 hours. The other steps are similar to those in Example 1. Wherein the recovery rate of the mixed alcohol is 99.0%, and the yield of TDA is 55% of the addition amount of waste residues.

Example 29

TDI tar solid waste residue particles, 1:1 mixture of diethylene glycol and heptanol, and potassium carbonate are mixed by a weight ratio of 28:50:22. Under stirring, after exhausting air by inputting nitrogen gas, the mixture is reacted at 130° C. in a sealed reaction vessel (0.15 MPa) for 14 hours. The other steps are similar to those in Example 1. Wherein the recovery rate of the mixed alcohol is 98.9%, and the yield of TDA is 46% of the addition amount of waste residues.

Example 30

TDI tar solid waste residue particles, 1:1 mixture of 1,2-propanediol and heptanol, potassium hydroxide, and water are mixed by a weight ratio of 15:60:15:10. Under stirring, after exhausting air by inputting nitrogen gas, the mixture is reacted at 130° C. in a sealed reaction vessel (0.2 MPa) for 14 hours. The other steps are identical with those in Example 1. Wherein the recovery rate of heptanol is 98.0%, and the yield of TDA is 41% of the addition amount of waste residues.

Example 31

TDI tar solid waste residue particles, 1:1:1 mixture of diethylene glycol, heptanol and glycol, sodium hydroxide, and water are mixed by a weight ratio of 15:60:15:10. Under stirring, after exhausting air by inputting nitrogen gas, the mixture is recirculated (normal pressure) and reacted at 140° C. for 14 hours. The other steps are identical with those in Example 1. Wherein the recovery rate of heptanol is 98.6%, and the yield of TDA is 45% of the addition amount of waste residues.

Since the present invention uses the aforementioned phase transfer catalysts for the hydrolysis reaction of TDI tar waste residues, the industrialized production can be realized under relatively mild conditions and TDA is recovered, thereby achieving the purpose of recycling of resources. The recovery rate of toluene diamine in the present invention is about 35-60% by weight of the amount of solid TDI tar waste residues with a high boiling point which are used for the hydrolysis, such that the amount of solid waste materials which are to be finally burned is reduced by 35-60%. The residual waste water and used phase transfer catalysts after the hydrolysis reaction in the present invention may be recycled, which improves the economy of the method, and moreover, the final solid waste materials would not further negatively impact the environment.

In conclusion, the present invention achieves highly efficient recovery of TDA under mild conditions, and makes itself have both practicability in industrial production and economic benefit and friendliness to the environment by recycling the waste water and used phase transfer catalysts.

The invention claimed is:

1. A method of recovering toluene diamine (TDA) from tar waste residues discharged from the synthesis process of toluene diisocyanate (TDI), comprising steps of:
   a) grinding the tar waste residues into particles;
   b) dispersing the particles of tar waste residues into a phase transfer catalyst, alkali and water to obtain a slurry, said phase transfer catalyst being selected from higher alcohols, polyols, polyether compounds or combinations thereof having a boiling point ranging from 120 to 280° C., wherein the weight percentage of the particles of tar waste residues is 10-30%, the weight percentage of the phase transfer catalyst is 40-75%, the weight percentage of the alkali is 10-30%, and the weight percentage of water is 0-25%;
   c) under the protection of a protective gas, subjecting the slurry to a hydrolysis reaction at a temperature of 120-180° C. under a meter-measured pressure of 0-0.95 MPa to produce toluene diamine, wherein the time for the hydrolysis reaction is 8 to 16 hours; and
   d) recovering toluene diamine from the hydrolysis reaction solution.

2. The method of claim 1, wherein the tar waste residues are ground into particles below 100 meshes.

3. The method of claim 1, wherein the protective gas is nitrogen gas.

4. The method of claim 1, wherein the alkali is sodium hydroxide, potassium hydroxide, or sodium carbonate, potassium carbonate.

5. The method of claim 1, wherein the slurry has a pH value of not less than 10.

6. The method of claim 1, wherein the phase transfer catalyst is selected from the group consisting of heptanol, diethylene glycol, glycol, 1,2-propanediol, 1,3-propanediol, 1,4-butanediol, hexanediol, and combinations thereof.

7. The method of claim 1, wherein the hydrolysis reaction is conducted in two or more reactors connected in series or in parallel.

8. The method of claim 1, wherein the hydrolysis reaction is conducted in a reactor which can be heated at a controllable temperature, in a stirring-allowable reactor, and/or in a sealed reactor or a reactor having a recirculation device.

9. The method of claim 1, wherein up to 99.6% of the phase transfer catalyst is recovered after step c).

10. The method of claim 1, wherein the phase transfer catalyst is recycled.

11. The method of claim 1, wherein 98.0% to 99.6% of the phase transfer catalyst is recovered.

* * * * *